United States Patent [19]

Reynolds et al.

[11] 4,269,387
[45] May 26, 1981

[54] NEEDLE VALVE AND METHOD OF MANUFACTURING A NEEDLE VALVE

[75] Inventors: Gordon S. Reynolds, Bountiful; Robert J. Todd, Salt Lake City, both of Utah

[73] Assignee: Sorenson Research Co., Inc., Salt Lake City, Utah

[21] Appl. No.: 62,872

[22] Filed: Aug. 1, 1979

[51] Int. Cl.³ .................. F16K 41/00; F16K 27/02
[52] U.S. Cl. .................................. 251/122; 251/215; 251/366; 251/DIG. 4; 264/230; 264/242; 264/274; 264/275; 264/237
[58] Field of Search ............... 251/122, 118, 366, 367, 251/368, 215, DIG. 4; 264/242, 274, 275, 230, 237

[56] References Cited

U.S. PATENT DOCUMENTS

| | | | |
|---|---|---|---|
| 2,173,979 | 9/1939 | Picut | 251/122 |
| 3,314,644 | 4/1967 | Dwyer et al. | 264/242 X |
| 3,434,694 | 3/1969 | Skinner | 251/215 |

FOREIGN PATENT DOCUMENTS 1359824  3/1964  France ..................... 251/366

*Primary Examiner*—Arnold Rosenthal

*Attorney, Agent, or Firm*—H. Ross Workman; Rick D. Nydegger; J. Winslow Young

[57] ABSTRACT

A needle valve and a method of manufacturing the needle valve. The needle valve has a metal needle with a leading end that is elongated and tapered so as to provide carefully restricted fluid flow along the length of the tapered end. A portion of the needle is threaded so that the position of the tapered end may be adjusted by screwing the needle. A housing for the needle is manufactured by placing the needle into a mold. The housing is then injection molded around portions of the metal needle. The molded housing forms an inlet port around the tapered end of the needle and a collar around the threaded portion of the needle. An outlet port is molded adjacent to the tapered end and is in fluid communication with the inlet port of the housing. As the housing cools, the plastic shrinks thus conforming the inlet port to the tapered end of the metal needle and creating a hermetic seal around the tapered end. A plastic knob is also molded onto the opposite end of the metal needle. The plastic knob may be rotated so that the tapered end of the needle may be screwed into or out of the inlet port of the plastic housing in order to control fluid flow therethrough.

38 Claims, 6 Drawing Figures

NEEDLE VALVE AND METHOD OF MANUFACTURING A NEEDLE VALVE

BACKGROUND

1. Field of the Invention

The present invention relates to valves for controlling fluid flow, and more particularly to a needle valve having particular application when low flow rates are desired, as for example when parenterally administering fluids to a patient.

2. The Prior Art

Parenteral administration of fluids to a patient has long been known in the medical art. A conventional parenteral administration system typically includes a container of liquid, an elongated flexible tube and a cannula or catheter that is inserted into the cardiovascular system of the patient. The liquid thus administered may be whole blood, plasma, or any one of a variety of medications.

In the past, infusion of parenteral fluids into a patient has been controlled by partially collapsing a portion of the delivery tube. This may be done with the use of a roller clamp or a pinch-type clamp. The rate of flow is then determined by counting the number of drops per unit of time that occur in a drip chamber.

This technique has proved satisfactory in most cases where desired flow rates are comparatively fast or where the accuracy of the flow rate is not particularly critical. However, there are some instances where greater control of the rate of infusion is of utmost importance. For example, when medication and fluids are administered to patients suffering from renal disorders, very low flow rates must be used and careful control of the flow rate is highly important.

Another example of an instance requiring more carefully controlled infusion at low flow rates includes the parenteral administration of medications by injecting the medication into an infusion fluid and then administering the infusion fluid over an extended period of time. Constant administration of parenteral fluids at very low flow rates has also been used to keep intravenous cannulas and catheters from becoming clogged during central arterial pressure monitoring.

The use of needle valves for obtaining more controlled flow of parenteral fluids is known in the art. Typically, prior art needle valves include a metal housing that is carefully machined to conform to an elongated, tapered needle that fits within the housing. A metal collar is also typically machined and fits onto the housing. The needle screws into the collar and the position of the needle may be adjusted by screwing the needle. Typically some type of gasket is placed over the needle to prevent leakage through the housing.

In the use of this type of needle valve it has been observed that high precision control of fluid flow at very low rates is not possible to achieve because of the difficulty of precisely machining the housing and tapered end of the needle in such a way that they will fit together with a very close tolerance.

More recent types of needle valves have been constructed by separately molding either the housing or the tapered needle and then assembling these components in the same manner as described above. Needle valves constructed in accordance with this method have also proved to exhibit the same difficulties when attempting to achieve precise control of fluids at very low flow rates.

In addition to the inaccuracies inherent with these kinds of devices, they are also relatively expensive to build because they require very detailed machining of metal parts. Although the cost is somewhat reduced with those types of devices which use some parts molded from plastic, the cost of producing the valves is still relatively high because they require additional labor and time to assemble all of the parts.

Accordingly, what is needed is a needle valve that is capable of achieving very precise control of fluid flow at low rates and which can be inexpensively manufactured.

BRIEF SUMMARY AND OBJECTS OF THE INVENTION

The needle valve of the present invention consists of a metal needle and a molded plastic housing for the needle. One end of the metal needle is tapered and is hermetically sealed in an inlet port provided in the housing. An outlet port is in fluid communication with the inlet port and is adjacent to the tapered end of the needle. The housing is further provided with a collar that is adapted to receive the threaded portion of the metal needle so that the needle may be adjusted to control fluid flow through the inlet port. Advantageously, because the tapered end of the metal needle is hermetically sealed in the inlet port along its entire length, very precise fluid control can be achieved at very low flow rates. The method of manufacture of the present invention includes inserting the needle into a mold and injection molding a unitary housing directly onto the metal needle. Thereafter, as the plastic cools it shrinks so as to conform to the tapered end of the needle, thus creating the hermetic seal along its length.

It is therefore a primary object of the present invention to provide an improved needle valve capable of accurately controlling fluid flow at very low rates.

Another object of the present invention is to provide a needle valve having a metal needle hermetically sealed in a unitary housing that is molded directly onto the needle so as to conform to the exterior of the tapered end of the needle.

Yet another object of the present invention is to provide a novel method of manufacturing a needle valve which eliminates the need for close machining tolerances or assembling procedures by insert molding a unitary housing onto a metal needle.

These and other objects and features of the present invention will become more fully apparent from the following description and appended claims taken in conjunction with the accompanying drawings.

4 prior to injection of the plastic material that forms the housing of the needle valve and knob.

Figure 6:
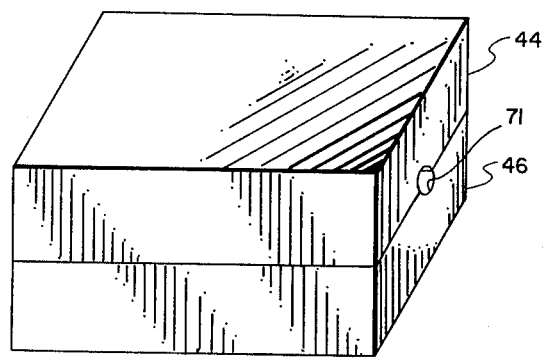

FIG. 6 is a perspective illustration of the molding as assembled and as used during the injection molding process.

DETAILED DESCRIPTION OF THE PREFERRED EMBODIMENTS

The invention is best understood by reference to the drawing wherein like parts are designated with like numerals throughout.

1. The Structure

Figure 1:
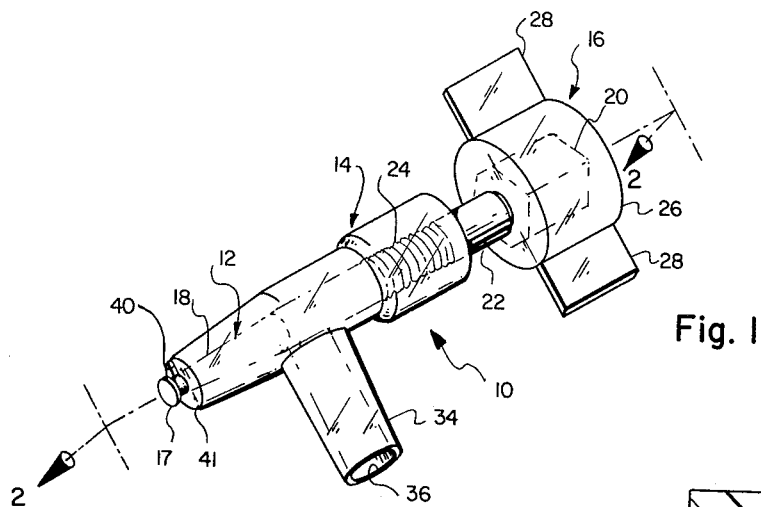
FIG. 1 is an enlarged perspective illustration of the needle valve of the present invention.

The needle valve of the present invention is generally designated at 10 in FIG. 1. Needle valve 10 consists primarily of three parts: a needle member generally designated 12, a unitary housing generally designated 14, and a knob generally designated 16.

Figure 2:
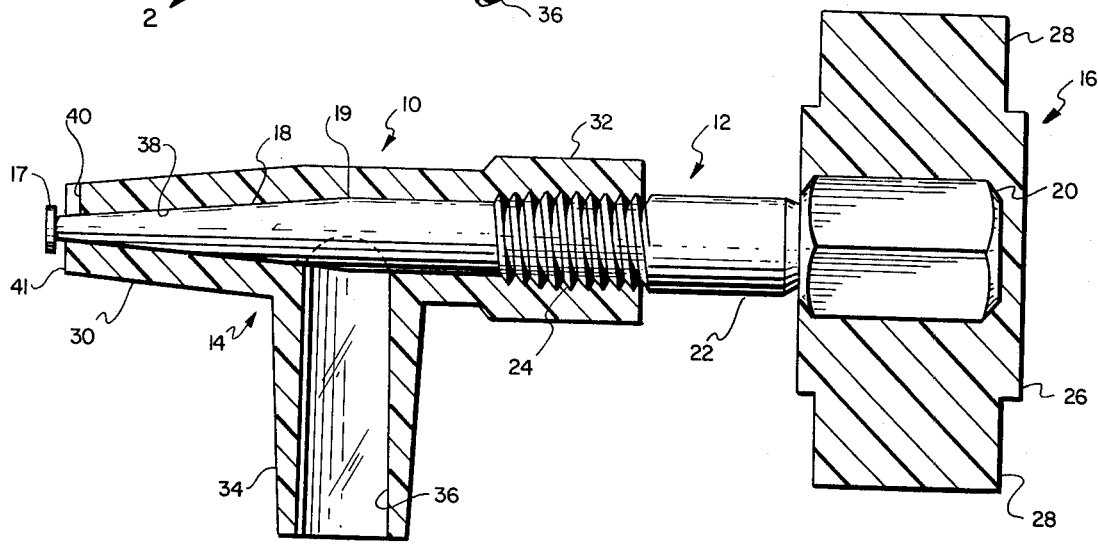
FIG. 2 is a cross-sectional view of the needle valve of FIG. 1 taken along line 2—2.

As shown best in FIG. 2, the needle member 12 has a leading end that is substantially elongated and tapered as at 18. The tapered end 18 protrudes slightly beyond the end 41 of housing 14 and terminates in an enlarged, flattened tip 17. Tip 17 prevents the needle member 12 from being completely withdrawn from housing 14. The trailing end of needle member 12 terminates in a head 20. Head 20 may be provided with any suitable shape so as to prevent the metal needle from slipping when knob 16 is turned. For example, in the illustrated embodiment head 20 is hexagonal. Between hexagonal head 20 and tapered end 18 is a shaft 22 that is provided with a threaded portion 24.

With further reference to FIG. 2, it will be seen that knob 16 is molded directly onto the hexagonal head 20 of needle member 12. Knob 16 has an enlarged, cylindrical base 26. Wings 28 are joined to the base 26 and extend therefrom so as to provide increased leverage for purposes of screwing the needle member 12 into or out of the housing 14. The hexagonal configuration of the head 20 helps to prevent slippage of the needle member 12 when the knob 16 is rotated.

Referring still to FIG. 2, housing 14 has an inlet port 30 that corresponds to the tapered leading end 18 of needle member 12. A small inlet channel 40 is formed in the side of end 41. Channel 40 is designed to permit fluid into throughbore 38 even when the enlarged tip 17 of needle 12 abuts against the end 41 of housing 14. A raise (not shown) could also be formed on end 41 for the purpose of insuring that fluid will flow past the tip 17 and into throughbore 38.

The opposite end of housing 14 terminates in a collar 32 that is molded onto the threaded portion 24 of needle member 12. Intermediate the collar 32 and inlet port 30 there is an outlet port 34. Inlet port 30 and outlet port 34 may be formed as conventional luer fittings that may be either male or female in their configuration and that may be readily interconnected to conventional fittings on the tubing of an I.V. administration set. Other configurations or connecting systems may also be used.

Throughbore 36 of outlet port 34 is positioned so that it is adjacent to the point 19 of shaft 22 where the taper begins. Thus, as soon as the tapered end 18 begins to be withdrawn through housing 14 a very small fluid passageway will be formed by throughbores 38 and 36. Fluid will flow into throughbore 38 of inlet port 30 and out the throughbore 36 of outlet port 34.

Fluid flow will not occur until point 19 (i.e. the point where the taper begins) reaches the throughbore 36 of outlet port 34. Thus, by placing the outlet port 34 adjacent to the point 19, and by making the tapered end 18 very long, very precise control of fluid flow can be achieved over a wider range of flow rates. Less control over fluid flow occurs if outlet port 34 is not adjacent the tapered end 18 because in order to permit fluid flow, tapered end 18 will have to be withdrawn a greater distance in order for the point 19 to reach throughbore 36.

Moreover, as hereinafter described in more detail, the degree of precision in controlling fluid flow through the inlet port 30 is significantly increased by insert molding the housing 14 directly onto the needle member 12. In this way, the needle member 12 will be hermetically sealed inside of the housing 14 and the housing 14 will exactly fit the tapered configuration of needle member 12, eliminating inaccuracies that would otherwise arise because of misalignment of the needle in the housing or because of unacceptable tolerances experienced when trying to machine the needle member 12 and housing 14.

2. The Method of Manufacture

Figure 3:
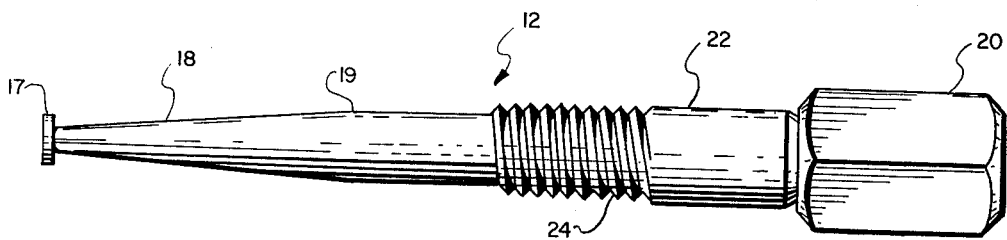
FIG. 3 is an enlarged side elevational view of the needle member used in conjunction with the needle valve of the present invention.

As shown in FIG. 3, the method of manufacturing the needle valve of the present invention begins by fabricating the needle member 12. In the illustrated embodiment, needle member 12 is preferably fabricated from metal, such as stainless steel. Since the needle member 12 is constructed from metal, it will not melt during the injection molding process described below. However, it will of course be appreciated that certain types of high temperature plastics or ceramics could also be used in accordance with the method of manufacture of the present invention.

Figure 4:
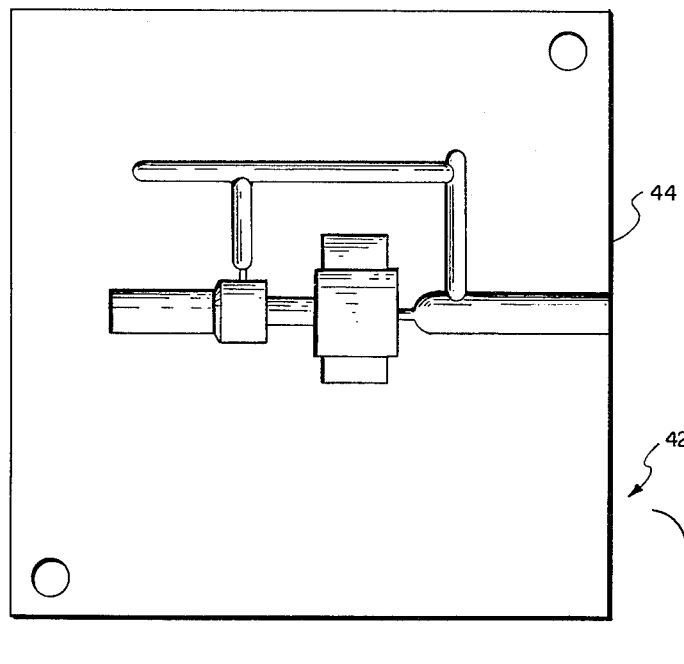
FIG. 4 is a top plan view of the mold used in conjunction with the method of manufacture of the present invention.
Figure 4:
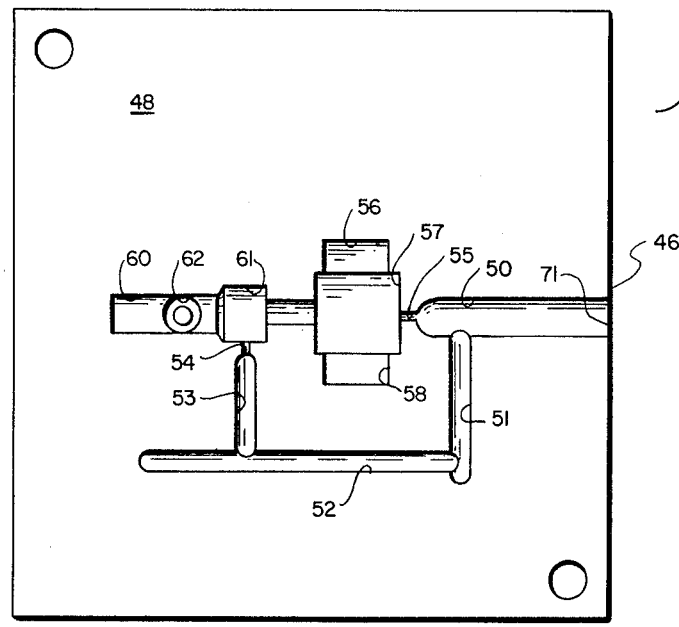

FIG. 4 illustrates the top and bottom portions of the mold generally designated 42 used to form the housing 14 and knob 16 of needle valve 10. The top half of mold 42 is illustrated at 44 and the bottom half is illustrated at 46.

Each half 44 and 46 is complimentary in its configuration so that when they are placed together, the desired configuration for the housing 14 and knob 16 will be formed therebetween. For ease of illustration and description, only the configuration of the half 46 will be described since the other half is complimentary in its configuration.

With continued reference to FIG. 4, each half of mold 42 has a series of channels 50-55 cut into its face 48. Molten plastic is injected through an opening 71 and is then conducted through the channels 50-55 to depressions 56-58 and 60-62 formed on face 48. Depressions 56-58 and 60-62 correspond to the different portions of housing 14 and knob 16 of the needle valve. Depressions 56-58 correspond to the rounded base 26 and wings 28 of the knob 16. Depressions 60 and 61 correspond to the inlet port 30 and collar 32 of housing 14, respectively. Annular channel 62 corresponds to the outlet port 34 of housing 14.

Figure 5:
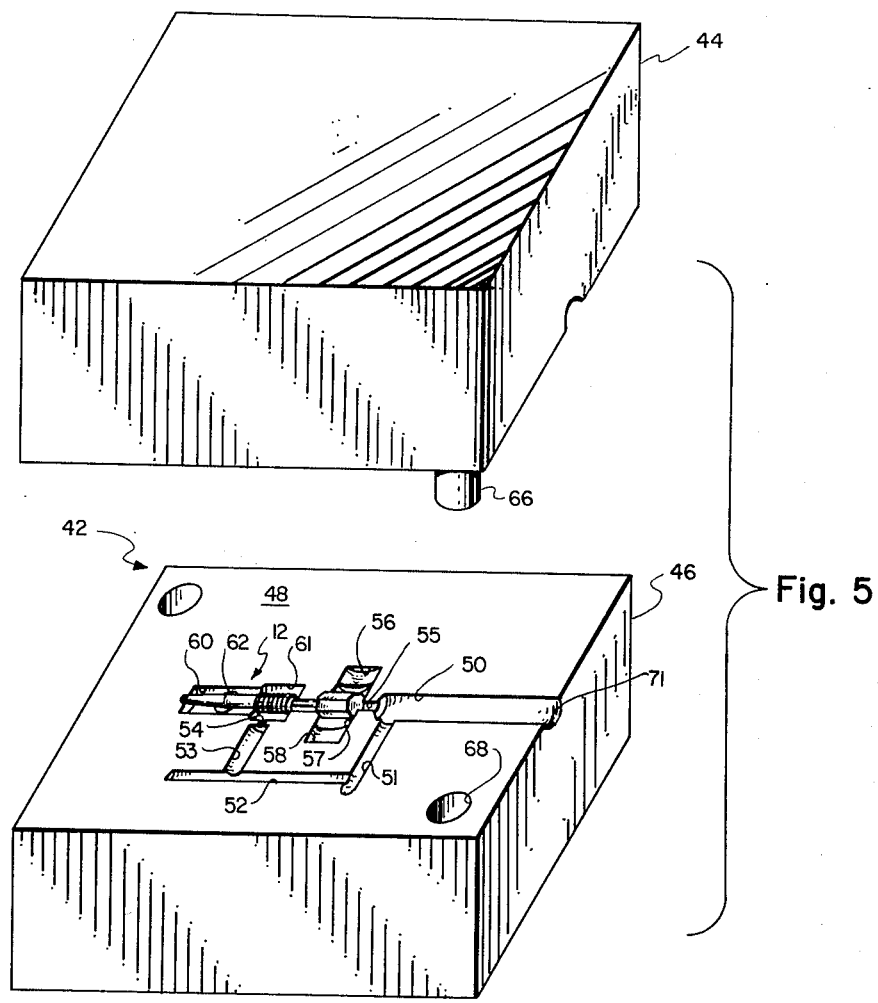
FIG. 5 is an exploded perspective view showing the needle member of FIG. 3 inserted into the mold of FIG.

As shown in FIG. 5, the metal needle member 12 is placed in the mold 42 and the pegs 66 on the top half 44 are inserted into the holes 68 provided on the face 48 of the bottom half 46. Molten plastic material is then injected through the opening 71 provided at the end of channel 50 (see also FIG. 4). The plastic material flows through the channels 50-55 (see also FIG. 4) into the depressions 56-58 that form the knob 16 and the depressions 60-61 and annular channel 62 that form the unitary housing 14. The plastic used for purposes of the injection molding can be any type of thermoplastic, as for example acrylic or styrene.

Significantly, the molten plastic flows into the mold 42 and is molded directly onto the metal needle member 12, thus ensuring that the housing 14 is configured so that it exactly fits the tapered end 18 of needle member 12. This advantageously eliminates any imprecision in the alignment between the tapered end 18 of needle member 12 and the throughbore 38 of inlet port 30, thus greatly increasing the precision with which fluid can be controlled at very low flow rates. Moreover, as the molten plastic cools, it will shrink and create a hermetic seal around the tapered end 18 and threaded portion 24 of needle member 12. This eliminates the need for gaskets and eliminates the expense involved in assembling the gaskets onto the needle member.

It should be further appreciated that the insert molding process described above eliminates the need for time-consuming and expensive assembly procedures or for carefully controlled tolerances during machining procedures. The method of the present invention therefore greatly reduces the cost involved in constructing the needle valve of the present invention.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters patent is:

1. A method of manufacturing a needle valve, the method comprising the steps of:
   obtaining a needle member, the needle member having a first tapered end and a second end with a threaded portion intermediate said first and second ends;
   inserting said needle member into a mold; and
   molding a housing for said needle member, the housing comprising a first port molded around at least a portion of the tapered end of said needle member, a collar portion molded around said threaded portion of said needle member, and a second port in fluid communication with said first port.

2. A method as defined in claim 1 further comprising the step of molding a channel extending from the exterior surface to the interior surface of said housing in a location adjacent said first port.

3. A method as defined in claim 1 further comprising the step of molding a knob member onto the second end of said needle member.

4. A method as defined in claim 3 wherein said steps of molding said housing and said knob member are essentially simultaneously performed.

5. A method as defined in claim 1 wherein said step of molding said housing comprises the step of molding said second port adjacent to at least a portion of the tapered end of said needle member.

6. A method as defined in claim 1 wherein said step of molding said housing comprises the step of molding said second port outwardly from said housing body.

7. A method as defined in claim 1 wherein said step of obtaining said needle member comprises the step of fabricating said needle member.

8. A method as defined in claim 1 further comprising the step of cooling said housing so that the housing will shrink, creating a seal wherever said housing has been molded around said needle member.

9. A method as defined in claim 8 wherein said seal is hermetic.

10. A method as defined in claim 1 wherein said step of molding may be accomplished by an injection molding process.

11. A method as defined in claim 1 wherein said housing comprises an injection molded, unitary member.

12. A method of manufacturing a needle valve, the method comprising the steps of:
    fabricating a needle member, the needle member having a first elongated end that is tapered, and a second end with a threaded portion intermediate said first and second ends;
    inserting said needle member into a mold;
    separating said first and second ends by a portion of said mold; and
    simultaneously molding a housing and a knob member onto portions of said needle member, said housing comprising a first port molded around at least a portion of the tapered end of said needle member, a collar portion molded around said threaded portion of said needle member, and a second port molded adjacent to at least a portion of the tapered end of said needle member, said knob member being molded onto said second end of said needle member.

13. A method as defined in claim 12 further comprising the step of molding a channel extending between the exterior surface and the interior surface of said housing at a location adjacent said first port.

14. A method as defined in claim 12 further comprising the step of cooling said housing so that the housing will shrink, creating a seal wherever said housing has been molded around said needle member.

15. A method as defined in claim 14 wherein said seal is hermetic.

16. A method as defined in claim 12 wherein the process of molding may constitute injection molding of a unitary housing.

17. A needle valve for regulating fluid flow into an adjacent area comprising:
    means for housing a fluid;
    a first aperture in aid housing means for permitting the passage of said fluid into the interior of said housing means;
    a second aperture in said housing means for permitting the passage of said fluid out from the interior of said housing means;
    means extending within said housing means for restricting the movement of said fluid wherein a portion of said restricting means additionally extends through said first aperture;
    a third aperture in said housing means for permitting the extension of said restricting means into said housing means;
    first securing means positioned on the interior surface of said housing means for securing said restricting means and regulating its position within said housing means;
    second securing means positioned on said restricting means and conformably connecting to said first securing means for securing said restraining means and regulating its position within said housing means; and
    means affixed to the extended end of said restricting means, adjacent to said first aperture, for preventing the withdrawal of said extended end of said restricting means into the interior of said housing means.

18. A needle valve as defined in claim 17 additionally comprising a channel extending between the interior and exterior surface of said housing means for permitting the continued passage of said fluid through said housing means when said first aperture is blocked by said withdrawal preventing means.

19. A needle valve as defined in claim 17 additionally comprising lever means attached to said housing means for use in gripping and applying force to rotate said housing means about said restraining means.

20. A needle valve as defined in claim 17 wherein said first and second securing means comprise threads which are conformably oriented to permit their interaction in securing said needle member within said housing.

21. A needle valve as defined in claim 17 wherein said first and second apertures are in fluid communication with each other.

22. A needle valve as defined in claim 17 wherein said restricting means comprises a needle member having a first tapered end and a second end, with said first tapered end extending through said first aperture, and said second end extending through said third aperture in said housing means.

23. A needle valve as defined in claim 22 wherein said needle member is preferably fabricated of a metal material, and wherein said housing means comprises a plastic housing molded onto portions of said metal needle member so as to be hermetically sealed around said portions of said needle member.

24. A needle valve as defined in claim 23 additionally comprising a collar molded onto said threaded portion of said needle member so that said tapered end may be withdrawn to permit fluid flow when said knob member is rotated.

25. A needle valve as defined in claim 22 further comprising a knob member affixed to said second end of said needle member.

26. A needle valve as defined in claim 22 wherein the interior wall of said housing means conforms to the portion of said needle member extended within said housing means, when said needle member is fully extended into said housing means.

27. A needle valve as defined in claim 22 wherein said second aperture is positioned adjacent to a portion of the tapered end of said needle member.

28. A needle valve comprising:
a needle member, said needle member having a first tapered end and a second end with a threaded portion intermediate said first and second ends;
a housing molded onto portions of said needle member, said housing comprising a first port sealed around at least a portion of said tapered end, a body molded around said threaded portion of said needle member, and a second port in fluid communication with said first port.

29. A needle valve as defined in claim 28 further comprising a channel extending between the interior surface and exterior surface of said housing and positioned adjacent said first port.

30. A needle valve as defined in claim 28 further comprising a knob member affixed to the second end of said needle member.

31. A needle valve as defined in claim 30 wherein said knob member may be plastic, and may be molded onto the second end of said needle member.

32. A needle valve as defined in claim 28 wherein said housing may be rotated about said needle member.

33. A needle valve as defined in claim 28 wherein said needle member is metal.

34. A needle valve as defined in claim 28 wherein said housing comprises a plastic housing formed by molding plastic material onto portions of said needle member.

35. A needle valve as defined in claim 28 wherein said second port is adjacent to at least a portion of the tapered end of said needle member.

36. A needle valve as defined in claim 28 wherein the tip of said tapered end is enlarged so as to limit withdrawal of said needle member from the housing, and wherein the first port of said housing comprises an inlet channel for providing fluid flow around said enlarged tip and into said inlet port.

37. A needle valve comprising:
a needle member having a first elongated end that is tapered and a second end, with a threaded portion intermediate said first and second ends; and
a housing, said housing comprising a first port molded onto at least a portion of said tapered end so as to be sealed around said tapered end, a collar molded onto the threaded portion of said needle member, and a second port in fluid communication with said first port, said second port being molded so that it is adjacent to at least a portion of said tapered end.

38. A needle valve comprising:
a needle member having a first elongated end that is tapered and that terminates in an enlarged tip and a second end that terminates in a head, said needle member further having a shaft intermediate said tapered end and said head, said shaft comprising:
a threaded portion;
a knob member molded onto the head of said member; and
a housing molded onto portions of said needle member so as to be sealed around said portions of said needle member, said housing comprising a first port molded around all but the tip of said tapered end, said first port comprising an inlet channel for providing fluid flow around the enlarged tip of said needle member, a collar molded onto said threaded portion so that said tapered end may be withdrawn to permit fluid flow when said knob is rotated, and a second port molded adjacent and normal to the tapered end of said needle member, said second port being in fluid communication with said first port.

* * * * *

UNITED STATES PATENT AND TRADEMARK OFFICE
CERTIFICATE OF CORRECTION

PATENT NO. : 4,269,387
DATED : May 26, 1981
INVENTOR(S) : Gordon S. Reynolds and Robert J. Todd It is certified that error appears in the above–identified patent and that said Letters Patent are hereby corrected as shown below:

Column 6, line 45: "in aid housing" should read "in said housing"

Signed and Sealed this

Eleventh Day of August 1981

[SEAL]

Attest:

Attesting Officer

GERALD J. MOSSINGHOFF

Commissioner of Patents and Trademarks